United States Patent
Fry et al.

(10) Patent No.: US 6,599,733 B1
(45) Date of Patent: Jul. 29, 2003

(54) MICROBIAL BIODEGRADATION OF PHOSPHONATES

(75) Inventors: Ilona J. Fry, Edgewood, MD (US); Joseph J. DeFrank, Bel Air, MD (US); James P. Earley, South Bend, IN (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/844,829

(22) Filed: Apr. 27, 2001

Related U.S. Application Data

(63) Continuation-in-part of application No. 09/207,902, filed on Dec. 7, 1998, now abandoned.

(51) Int. Cl.[7] .................................................. C12N 1/20
(52) U.S. Cl. ...................... 435/252.4; 435/42; 435/244; 435/262.5; 424/93.3
(58) Field of Search ................................ 435/252.4, 42, 435/244, 262.5; 424/93.3

(56) References Cited

PUBLICATIONS

Munro, et al., Environmental Health Perspectives, (Dec., 1999) vol. 107, No. 12, pp. 933–974.*
Ohtake et al., Resources Conservation and Recycling, (1996) vol. 18, No. 1–4, pp. 125–134.*
Autenrieth, et al., In Situ and On–Site Bioremediation, Papers from the International In Situ and On–Site Bioremediation Symposium, 4th, New Orleans, Apr. 28–May 1, 1997, vol. 5, 49–54 Publisher: Battelle Press, Columbus, Ohio.*
Zhang, et al., Biotechnology and Bioengineering (1999), 64(2), 221–231.*

* cited by examiner

Primary Examiner—Irene Marx
(74) Attorney, Agent, or Firm—Ulysses John Biffoni

(57) ABSTRACT

A biodegradation process for the organophosphonate product of Sarin (O-isopropyl methylphosphonofluoridate) hydrolysis, i.e., isopropylmethylphosphonate (IMPA). This process provides a feasible biodegradation demilitarization alternative to Sarin incineration. Public opposition of nerve agent incineration is widespread, and alternative methods are sought to help the U.S. Army meet the 2007 demilitarization deadline imposed by the Chemical Weapons Convention. This process uses a two-step approach to IMPA biodegradation. In the first step, a concentrated IMPA solution is used as the sole nutritional carbon and phosphorus source for microbial cultures. The second step involves diluting the culture and adding an inexpensive carbon source to encourage bacterial phosphate assimilation. The biodegradation typically involves a consortium of microorganisms comprising *Methylobacterium radiotolerans* GB21, *Agrobacterium tumefaciens* GB2GA, *Klebsiella oxytoca* GB2CS, GB272, *Aureobacterium* sp. GB2 and three bacterial isolates belonging to the same species GB23, GB272, and GB292.

3 Claims, 5 Drawing Sheets

MICROBIAL BIODEGRADATION OF PHOSPHONATES

CROSS REFERENCE TO RELATED APPLICATION

This application is a Continuation-In-Part of application Ser. No. 09/207,902, filed Dec. 7, 1998 now abandoned.

GOVERNMENTAL INTEREST

The invention described herein may be manufactured, used and licensed by or for the U.S. Government.

FIELD OF THE INVENTION

The invention relates to the biodegradation of phosphonate products. In particular, this invention is a biodegradation process for the organophosphonate product of Sarin (O-isopropyl methylphosphonofluoridate) caustic hydrolysis, namely, isopropylmethylphosphonate (IMPA). This process provides a feasible biodegradation demilitarization alternative to Sarin incineration. Public opposition of nerve agent incineration is widespread, and alternative methods are sought to help the U.S. Army meet the 2007 demilitarization deadline imposed by the Chemical Weapons Convention.

BACKGROUND OF THE INVENTION

In view of the public outcry against the incineration of stockpiles of chemical agents, the U.S. Army is seeking alternative chemical agent demilitarization technologies. Microbial biodegradation is one promising alternative the Army is considering for this purpose. Recently, microbial biodegradation of hydrolyzed mustard (bis-2-chlorethyl sulfide) was sanctioned as the most promising alternative technology suitable for the Army's demilitarization goals for that chemical agent. See Irvine, D. A., J. P. Earley, D. P. Cassidy and S. P. Harvey, "Biodegradation of Sulfur Mustard Hydrolysate in the Sequencing Batch Reactor," Water Sci. and Tech. 35: 67–74 (1996), incorporated herein by reference in its entirety.

As other chemical warfare agents have different structures, the biodegradation of these materials and/or their neutralization products were pursued. The organophosphorus nerve agents VX (O-ethyl-S-2(diisopropylaminoethyl) methylphosphonothioate) and Sarin (O-isopropylmethylphosphofluoridate) represent a large portion of the Army's stockpile. Equimolar mixtures of VX and water undergo a slow (30–50 days at room temperature) auto-catalytic reaction resulting in cleavage of the P-S bond

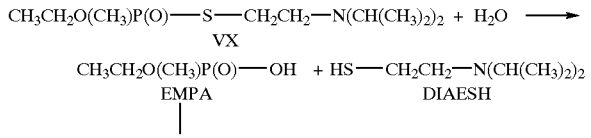

to produce ethylmethylphosphonate (EMPA) and DIAESH (Diisopropylaminoethylmercaptan).

Caustic hydrolysis of Sarin also produces an alkyl phosphonate:

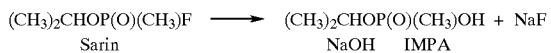

specifically, isopropylmethylphosphonate (IMPA) and sodium fluoride.

As is seen, the phosphonate products of chemical hydrolysis are similar for these two agents: ethylmethylphosphonate (EMPA) is the byproduct of VX hydrolysis and isopropylmethylphosphonate (IMPA) is the byproduct of the hydrolysis of Sarin. In the past, biodegradation of these materials was accomplished using strategies similar to that for mustard—sequencing batch reactors. The reactors in a sequencing batch reactor system operate through a cycle of four discrete periods. The periods are fill, react, settle and draw. Waste is introduced into the reactor during fill. In such cases, the byproduct phosphonates were used as the sole phosphorus source for growth. Supplementary glucose was supplied simultaneously with the hydrolyzed agent. Although EMPA biodegradation proceeded well for the VX hydrolysate using sequencing batch reactors (DeFrank, J. J., I. J. Fry, J. P. Earley and R. L. Irvine, Biodegradation Studies with Water-Hydrolyzed Nerve Agent VX. Proceedings of the 20$^{th}$ Army Science Conference, p. 555–559 (1996), incorporated herein by reference in its entirety), poor results were exhibited for IMPA biodegradation when sludge sequencing batch reactors were employed for the Sarin hydrolysate (DeFrank, J. J., I. J. Fry, C. M. Frost and J. P. Earley, Sequencing Batch Reactor Biodegradation of Water-Hydrolyzed Sarin, Proceedings of the 1996 ERDEC Scientific Conference on Chemical and Biological Defense Research, p. 361–367 (1996), incorporated herein by reference in its entirety). Clearly, a better approach was needed to effectively degrade the IMPA needed for Sarin demilitarization purposes.

Prior work on alkylphosphonate biodegradation was reported by several investigators (Wanner, B. L, Phosphate-Regulated Genes for the Utilization of Phosphonates in Members of the Family *Enterobacteiaceae*, In: Phosphate in Microorganisms: Cellular and Molecular Biology, A. Torriani-Gorini, E. Yagil and S. Silver eds. ASM Press, Washington, D.C., pp. 215–221 (1994), incorporated herein by reference in its entirety). However, almost all of these reports focused on the mono-substituted phosphonates, such as methylphosphonate (MPA), ethylphosphonate (EPA), or α-aminoethylphosphonate (AEPN). The enzyme responsible for MPA biodegradation is C-P lyase. The reaction catalyzed by this enzyme is:

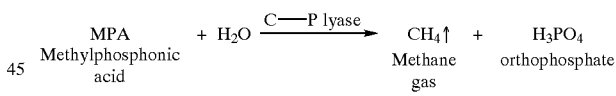

C-P lyase is inhibited by low levels of phosphate (Daughton, C. G., A. M. Cook and M. Alexander, Bacterial Conversion of Alkylphosphonates to Natural Products via Carbon-Phosphorus Bond Cleavage, J. Agric. Food Chem. 27: 1375–1382 (1979)).

The biochemistry of MPA biodegradation has been well characterized in Enterobacter, *Salmonella* and *E. coli* (Wanner, B. L, Phosphate-Regulated Genes for the Utilization of Phosphonates in Members of the Family *Enterobacteriacca*, In: Phosphate in Microorganisms: Cellular and Molecular Biology, A. Torriani-Gorini, E. Yagil and S. Silver eds. ASM Press, Washington, D.C., pp. 215–221 (1994), incorporated herein by reference in its entirety). Several genes for MPA uptake and the biodegradation pathway were cloned and expressed in *E. coli* (Wanner, B. L. and J. A. Boline, Mapping and Molecular Cloning of the phn (psiD) locus for phosphonate utilization in *Escherichia coli*. J. Bacteriol. 172: 1186–1196(1990), incorporated herein by reference in its entirety). IMPA biodegradation was reported in intracellular extracts of

*Pseudomonas testosteroni* (Daughton, C. G., A. M. Cook and M. Alexander, Bacterial Conversion of Alkylphosphonates to Natural Products via Carbon-Phosphorus Bond Cleavage, J. Agric. Food Chem. 27: 1375–1382 (1979)). This organism could use several disubstituted alkylphosphonates as its sole phosphorus source but not as a sole carbon source.

SUMMARY OF THE INVENTION

Thus, an object of this invention is to provide a consortium of microorganisms which use disubstituted phosphonates as a sole carbon and phosphorus source, thereby effectively degrading said phosphonates.

The present invention is a defined aerobic bacterial consortium and process that degrades the organophosphonate product of Sarin (O-isopropyl methylphosphofluoridate) hydrolysis, namely isopropylmethylphosphonic acid (IMPA). The hydrolyzed Sarin (GBH) stock solutions that were the feed source for this invention contained 4% hydrolyzed Sarin (40 g/l) in sodium hydroxide; hence a feed of 80 ml/l GBH is actually 3.2 g/l IMPA. Initial concentrations of alkylphosphonates of from about 2.1 to 4.2 g/l can be used.

The invention degrades IMPA to methyl phosphonic acid (MPA) in the presence of equimolar fluoride ion. Isopropanol released from this reaction supplies the sole carbon source for the culture. Furthermore, the consortium degrades MPA to liberate methane and inorganic phosphate. The consortium utilizes the phosphate produced from this reaction as a sole phosphorus source. Another compound metabolized in an analogous manner by the invention is ethylmethylphosphonic acid (EMPA), one of the hydrolysis products of VX (O-ethyl-S-2(diisopropylaminoethyl) methylphosphonothioate). This was observed during bibdegradation studies of hydrolyzed Sarin (GBH), as EMPA is a minor contaminant of this preparation. The biodegradation of combined organophosphonates (EMPA, IMPA and MPA) is a characteristic of the present invention.

Thus, the invention is a defined consortium of several bacteria capable of biodegrading combined organophosphonates. These organisms have been identified or characterized and their role in hydrolyzed Sarin biodegradation defined. None of the organisms identified in this consortium have any prior published description of phosphonate biodegradation. The ability of this consortium to utilize hydrolyzed Sarin as a sole carbon and sole phosphorus source is a novel ability not previously reported for a bacterial isolate or a defined consortium.

The invention employs a process involving two bioreactors. The process comprises contacting an aqueous alkylphosphonate solution and the GB2 consortium in a first bioreactor, wherein the alkylphosphonate solution provides the sole nutritional sources of carbon and phosphorus to the bacteria under aerobic conditions; transferring the culture to a second bioreactor once the enzymatic conversion of the alkylphosphonate to MPA is complete; diluting the culture with GBMH medium; and adding a carbon source in a concentration sufficient to allow the culture to grow under aerobic conditions and thereby converting the MPA to phosphate which is utilized for growth and energy. At this point the process is complete, i.e., all of the alkylphosphonates are mineralized meeting international treaty requirements, and the contents of the second reactor can be discarded.

This invention plays a key role in the bioprocess demilitarization of the nerve agent Sarin. Microbial degradation of waste chemicals is an environmentally-compatible, relatively low cost treatment technology that has a proven track record and enjoys wide public acceptance. This invention should find applications in the biodegradation of both U.S. and foreign chemical agent stockpiles.

BRIEF DESCRIPTION OF THE DRAWING

The drawing consists of multiple figures, in which.

DETAILED DESCRIPTION OF THE PREFERRED EMBODIMENTS

Figure 1:
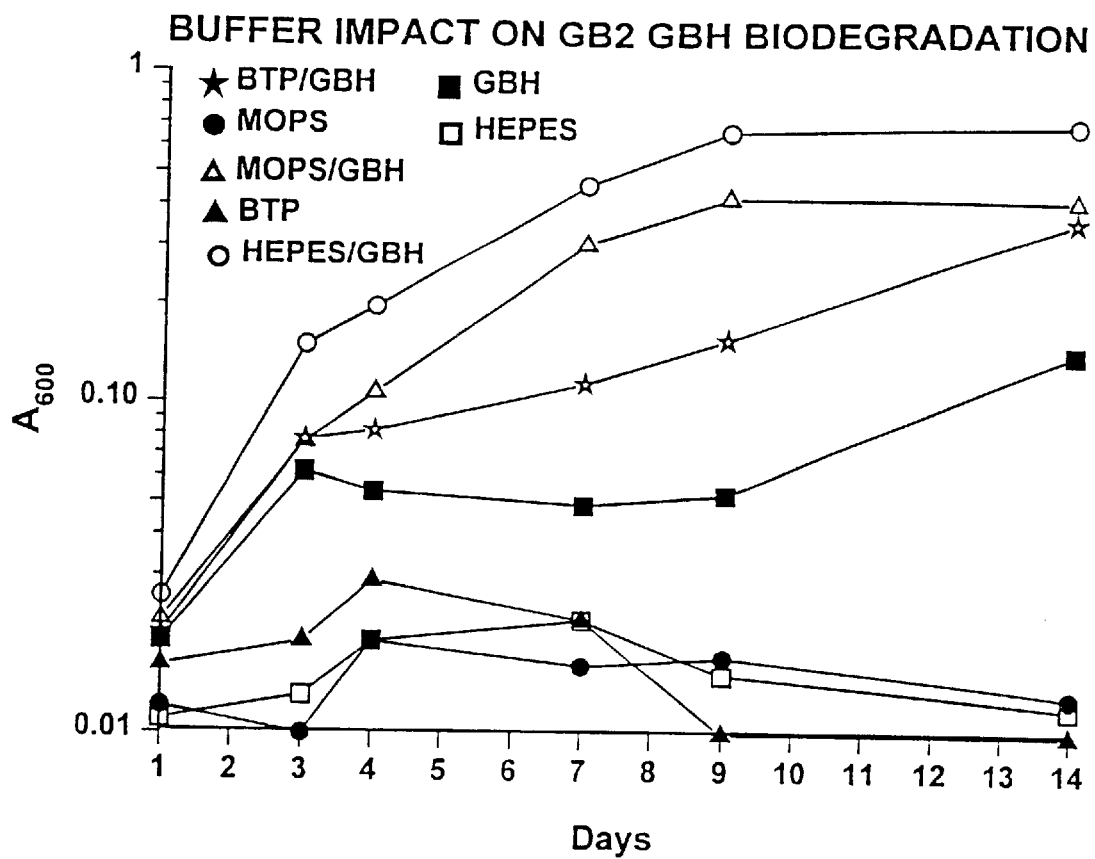
FIG. 1 shows the effect of various Good Buffers on the growth of GB2 microorganism consortium on GBH (hydrolyzed Sarin (GB)); Growth was monitored turbidimetrically at 600 nm in tubes with a path length of 1.8 cm. The buffer composition of the growth medium (GBM) is indicated by the symbols provided in the figure. The buffer concentration in all cases was 50 mM. The initial organophosphonate concentration was 3.2 g/l (24 mM or 80 ml/l hydrolyzed Sarin).
Figure 2:
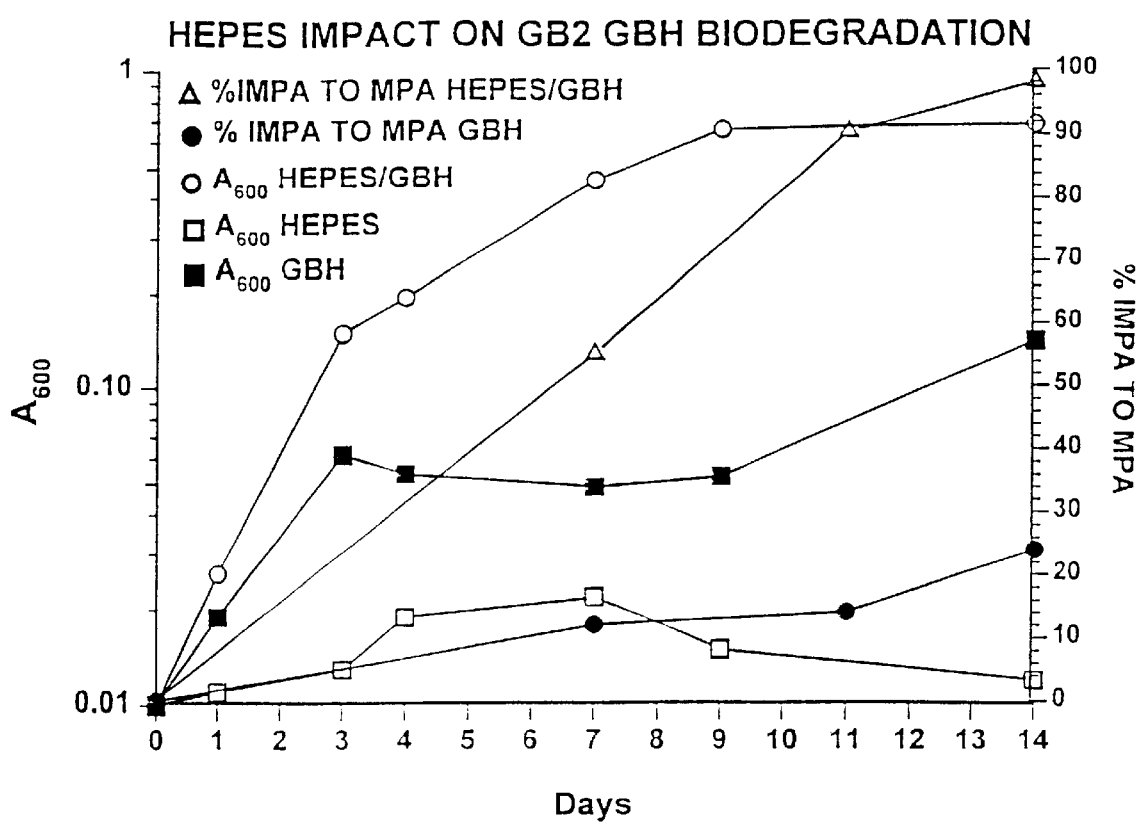
FIG. 2 compares GB2 growth and IMPA to MPA conversion with HEPES as the buffer supplied in the GBM medium. Buffer concentration for these 5 ml tube cultures in all cases is 50 mM with a starting pH of 7.0. OP mineralization was monitored by CGC/FPD-P and compared to an uninoculated sample. The data points plotted for %IMPA to MPA conversion represent the amount of IMPA at the start of the experiment which was converted to MPA after the indicated number of days after inoculation. Growth was monitored turbidimetrically at 600 nm ($A_{600}$) as in FIG. 1 and those data points are indicated in the figure. Again, the initial concentration of the organophosphonate was 3.2 g/l (24 mM or 80 ml/l hydrolyzed Sarin).
Figure 3:
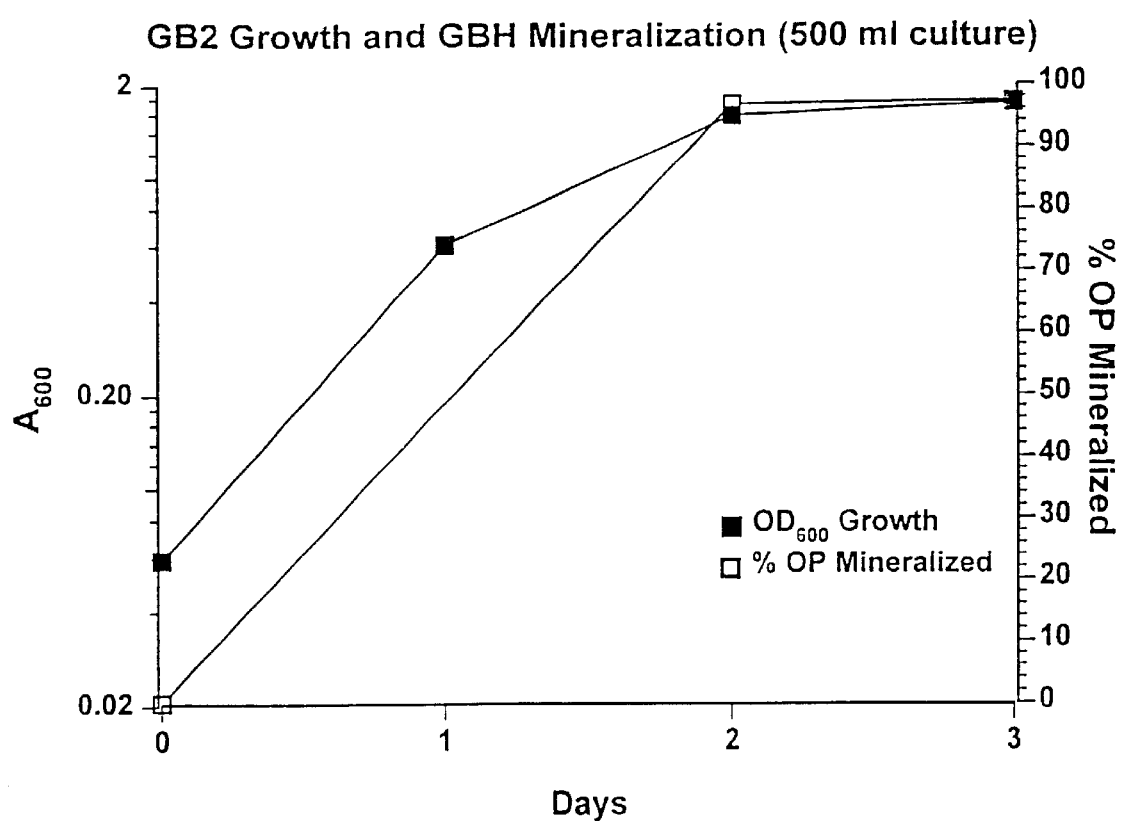
FIG. 3 shows the growth of GB2 and concurrent mineralization of GBH for a 500 ml flask culture. Growth was monitored turbidimetrically at 600 nm ($A_{600}$) as in FIG. 1 and those data points are indicated in the figure by solid squares. The starting organophosphonate concentration was 2.3 mM and the supplemental carbon source was corn syrup supplied at 20 g/l. The culture was buffered with 50 mM HEPES, pH 7.2. OP mineralization was monitored by CGC/FPD-P and compared to the sample taken at the start of incubation. The % OP mineralized results are shown by the open squares.
Figure 4:
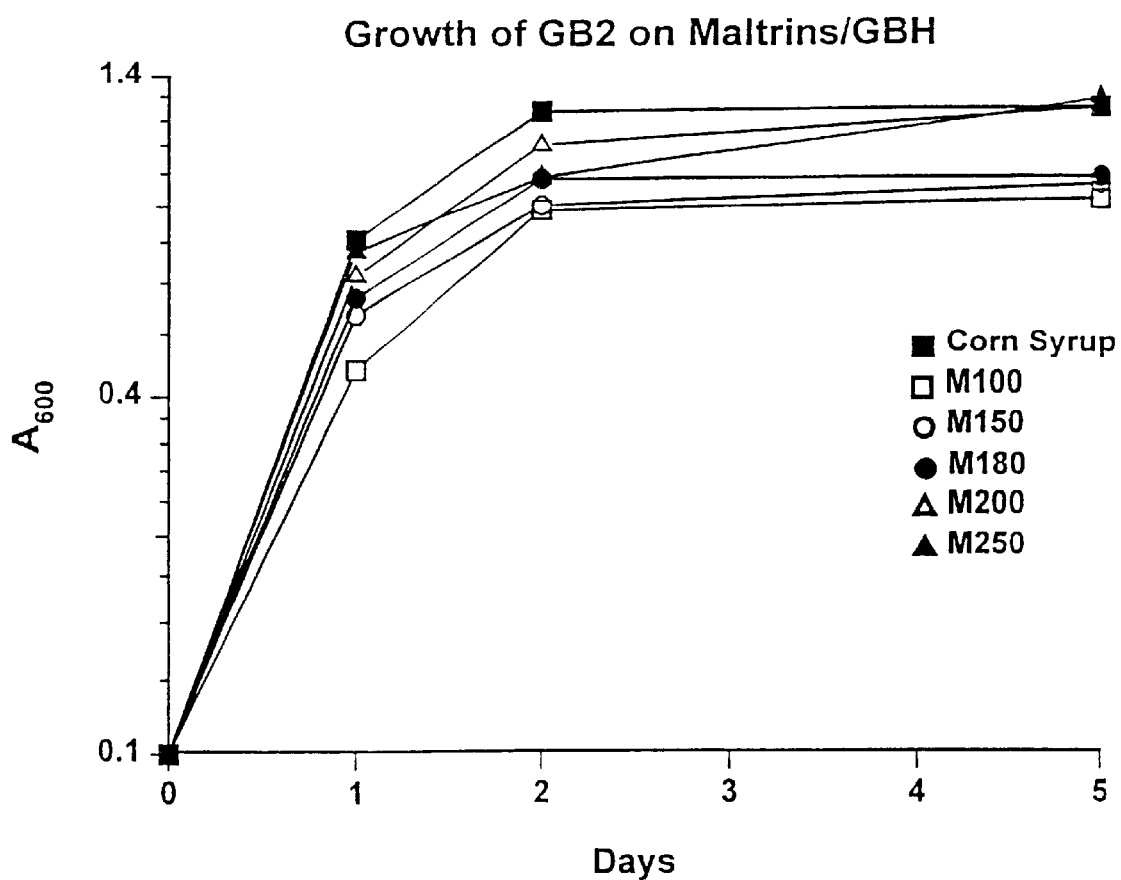
FIG. 4 compares the growth of the GB2 consortium with corn syrup and corn syrup solids (MALTRINS) as the supplemental carbon source in 5 ml cultures. All supplementary carbon sources were supplied at a concentration of 20 g/l. Growth, monitoring and culturing conditions were as indicated in FIG. 3. Data points for each of the cultures are as indicated in FIG. 4.
Figure 5:
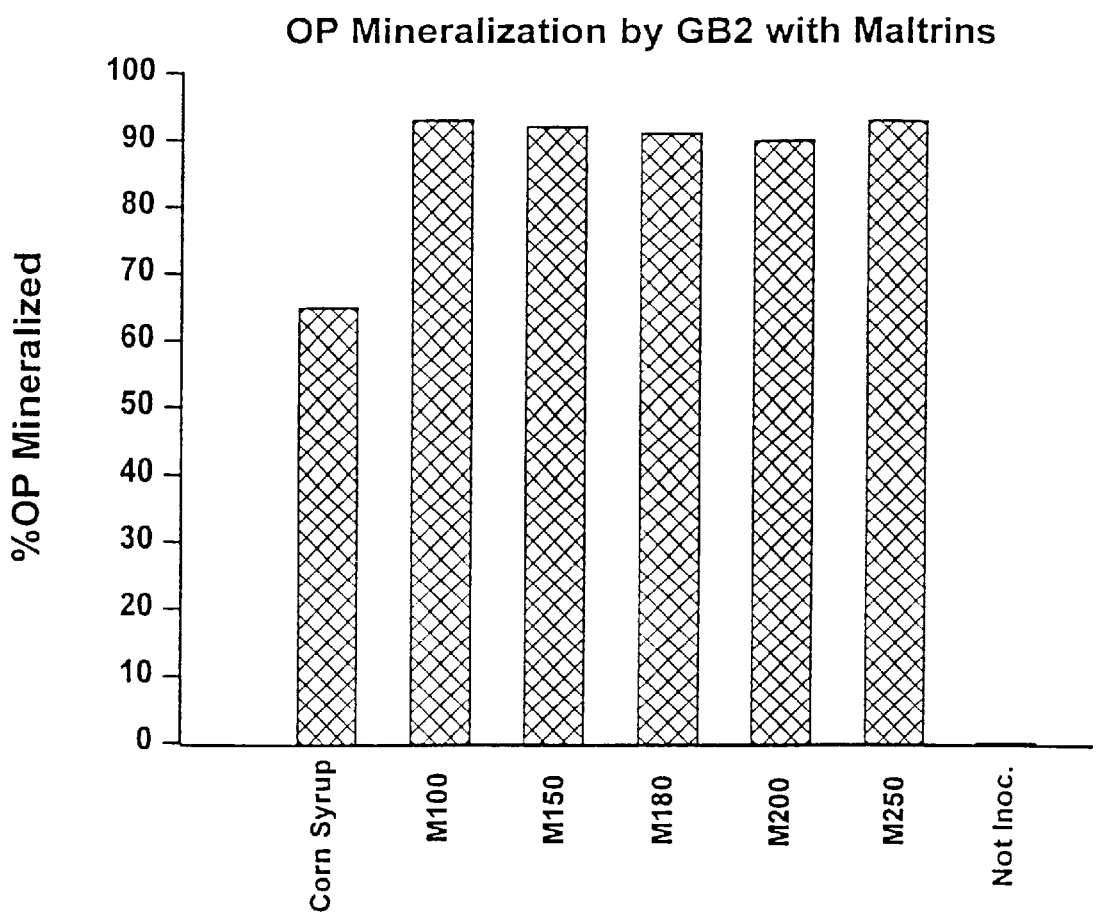
FIG. 5 compares the % OP mineralization by the corn syrup and MALTRIN cultures of FIG. 4. Organophosphonates were detected as in FIG. 2.

The present invention is a defined aerobic bacterial consortium (GB2) that degrades EMPA and/or the organophosphonate product of Sarin hydrolysis (IMPA) and a process of using this consortium for EMPA and/or IMPA biodegradation. The phosphonate byproduct of Sarin (O-isopropyl methylphosphofluoridate) hydrolysis is isopropylmethylphosphonic acid (IMPA). The present invention provides the means for a feasible biodegradation demilitarization alternative to Sarin incineration. Public opposition of nerve agent incineration is widespread, and alternative methods are sought to help the U.S. Army meet the 2007 demilitarization deadline imposed by the Chemical Weapons Convention.

The GB2 consortium was deposited on Feb. 18, 1999, with the ATCC, 10801 University Blvd., Manassas Va. 20110-2209, under Accession number 202200. The GB2 consortium was described as a defined consortium made up of the following organisms: *Methylobacterium radiotolerans* GB2 1; *Klebsiella oxytoca* GB2CS; *Agrobacterium tumefaciens* GB2GA; Aureobacterium GB2; and three unidentifiable bacterial isolates belonging to the same species, GB23, GB292, and GB272. The process employing the consortium GB2 uses a two-step approach to IMPA degradation. In the first step, a concentrated IMPA aqueous solution is used as the sole nutritional carbon and phosphorous source for microbial cultures.

This consortium, GB2, utilizes IMPA as its sole nutritional carbon and phosphorus source. The biodegradation of IMPA by GB2 follows the pathway:

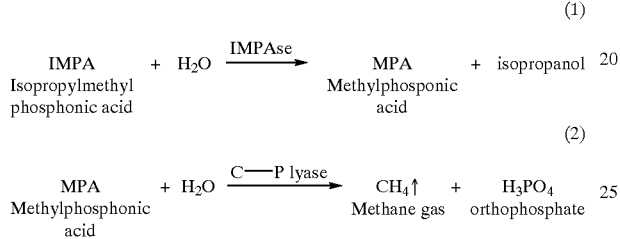

(1)

$$\underset{\text{Isopropylmethyl phosphonic acid}}{\text{IMPA}} + H_2O \xrightarrow{\text{IMPAse}} \underset{\text{Methylphosponic acid}}{\text{MPA}} + \text{isopropanol}$$

(2)

$$\underset{\text{Methylphosphonic acid}}{\text{MPA}} + H_2O \xrightarrow{\text{C—P lyase}} \underset{\text{Methane gas}}{CH_4\uparrow} + \underset{\text{orthophosphate}}{H_3PO_4}$$

Isopropanol released from the first reaction (1) provides the primary carbon source for the consortium. The inorganic phosphate resulting from the hydrolysis of MPA during the second reaction (2) provides the sole phosphorous source.

The second step in the process involves diluting the original products from step 1 and adding an inexpensive carbon source, such as corn syrup solids (CSS), corn syrup, or glucose. The additional carbon increases the demand for phosphorus required for microbial growth and maintenance and drives MPA mineralization. MPA serves as the sole phosphorus source and the corn syrup solids, in this example, the primary carbon source. Aeration releases methane gas from the exhaust vent of the bioreactor.

Two reactors are needed for the process. The first step of the biodegradation of phosphonates, the enzymatic conversion of IMPA to MPA by reaction (1), occurs in the first bioreactor. MPA released by the bacteria into the first bioreactor's effluent is transferred to the second bioreactor for its enzymatic conversion to inorganic phosphate and subsequent assimilation by the bacteria for growth and maintenance, as shown in reaction (2).

This process currently utilizes an initial concentration of hydrolyzed Sarin of about 60 to about 120 milliliters per liter, typically about 80 ml/l in the first reactor. For the second reactor, the effluent from the first reactor is diluted about 1:10 and enough carbon source material (CCS, corn syrup or glucose) added to consume the phosphate released from reaction (2) to provide at least 100:1 excess of carbon to phosphorus. The hydraulic residence time of the IMPA-containing solution in the first reactor is from about 3 days to 7 days and the hydraulic residence time of the diluted MPA-containing solution in the second reactor is from about 48 to about 72 hours. The temperature in both bioreactors ranges from about 28–29° C. The reactors are operated under aerobic conditions.

The microorganisms useful for biodegradation of combined organophosphonates comprise a consortium of microorganisms known as the GB2 consortium, comprising *Methylobacterium radiotolerans* GB2 1; *Klebsiella oxytoca* GB2CS; *Agrobacterium tumefaciens* GB2GA; Aureobacterium GB2; and three unidentifiable bacterial isolates belonging to the same species, GB23, GB292, and GB272.

Batch mode feeding and operation (A) of both steps of the process can be utilized, or a continuous first step and a batch second step (B). CSTRs (continuous stirred tank reactors) can be used for these operations, but immobilized cell, sequencing batch reactor or fixed film systems can be used for the first reaction (1). The latter strategies combined with the continuous first step and batch second step of feeding mode (B) are useful because biomass will accumulate as a biofilm in the first reactor, and this will shorten the hydraulic residence time needed to complete reaction (1). As reaction (1) is inherently slower than reaction (2) when the second reactor is supplied with a high-yield carbon source such as CSS, the shortest overall hydraulic residence time is obtained using this operational strategy.

This process is novel because it provides for substantial biodegradation of IMPA (>90%) where IMPA is the sole carbon and sole phosphorous source in its first stage.

The only precedent known to the inventors for this process was a single reactor sequencing batch reactor scheme previously tested by the inventors utilizing IMPA as the sole phosphorus source and supplementary glucose as the carbon source in a single stage process. As the metabolic demand for phosphorus is much lower than that of carbon, the present invention process gives superior IMPA biodegradation with a hydrolyzed Sarin concentration 15 times higher in a shorter period than what was seen in the single batch reactor, SBR system. The two reactor process of the present invention is clearly superior in performance, treatment time and in its ability to degrade much higher concentrations of hydrolyzed Sarin.

EXAMPLES

In the examples, as applicable, organophosphonates mineralized or converted by the invention were detected after drying and subsequent derivatization with TMCS by capillary gas chromatography using a flame photometric detector in phosphorus mode (CGC/FPD-P). All samples were run against uninoculated or untreated controls in duplicate. Data shown in the figures are the averages of duplicate analyses.

Example 1

Preparation of the GB2 Consortium

The GB2 consortium is composed of the following bacteria:

*Methylobacterium radiotolerans* GB21

Agrobacterium tumefaciensGB2GA

*Klebsiella oxytoca* GB2CS

GB272

*Aureobacterium* GB2

GB23

GB 292

GB23, GB292, and GB272 are unidentified organisms, but their physiological descriptions are reported in TABLE 1.

TABLE 1

| Characteristics of the Unidentified Bacteria of the GB2 Consortium | | | | | | |
|---|---|---|---|---|---|---|
| Isolate | Gram | Cellular Morph. | Colony Morph. | Oxidase | Catalase | Media Growth |
| GB272 | – | Cocco-bacillus | 0.5 mm white | + | – | TSA, MPAG, GBMH GBH |
| GB23 | – | Cocco-bacillus | 0.5 mm white | + | – | TSA, MPAG, GBMH GBH |

TSA = Trypticase Soy Agar
GBMH = GBM buffered with 50 mM HEPES
MPAG = GBMH + 2.30 mM MPA + 20 g/l glucose
GBMH GBH = GBMH + 80 ml/L GBH
GB2CS4 belongs to the Aureobacterium genus and has been identified as Aurobacterium sp. GB2

All of these organisms were derived from cultures selected for their ability to use IMPA as a sole carbon/phosphorus source. Sequencing batch reactors degrading hydrolyzed VX or Sarin as a sole phosphorus source served as the inoculum for these enrichments. These reactors operated continuously for several months or years under specific conditions which forced the resident microbial population to evolve specialized processes for organophosphonate biodegradation. Thus, this inoculum can not be considered a naturally-occurring population.

The GB2 consortium biodegraded hydrolyzed GB (GBH) as the sole carbon and phosphorus source under aerobic culturing conditions at 28–29° C. when provided at a concentration of 80 ml/l. The growth medium used for the enrichment and subsequent biodegradation analysis was GBM. GBM is a phosphate-free aqueous medium composed of 0.5 g/l KC1, 0.5 g/l $NH_4SO_4$, 10 ml/l Wolin Salts, final pH 7.2. Organophosphonate substrates (e.g. GBH, MPA, etc.) were added to a final concentration of 2.7 mM. The GB2 consortium was obtained by successive culturing and transfer to fresh GBM, following the initial inoculation from the GBH and VXH sequencing batch reactors and digester. In this manner, only those organisms capable of utilizing IMPA or MPA as their sole carbon/phosphorus source resulted from these enrichment culture procedures. Biodegradation of hydrolyzed Sarin by the GB2 consortium is greatly enhanced in the presence of the piperazine-alkylsulfonic acid class of Good Buffers, such as HEPES. When these buffers are provided at a starting pH of 7.0 and a concentration of 50 mM, IMPA biodegradation is greatly improved in terms of both the time required and the degradation rate compared to unbuffered cultures. Studies using these buffers as sole carbon sources show that they themselves are not metabolized by the consortium (FIG. 1 and 2).

As biodegradation of IMPA as the sole phosphorus and carbon source was not reported in bacterial isolates, the evidence presented here represents a novel finding. Three of the consortium members, GB23, GB272 and *Methylobacterium radiotolerans* GB21, have this ability. These three organisms and the other members of the consortium degrade MPA to methane and inorganic phosphate. The abilities of the combined members of this consortium result in excellent IMPA to MPA biodegradation (>90%) when carried out under the conditions and parameters set forth hereinafter. FIG. 2 illustrates the relative impact of HEPES on GB2 GBH biodegradation.

Example 2

IMPA mineralization is also possible with GB2, if an additional carbon source is supplied after IMPA conversion to MPA is complete. This was demonstrated in lab-scale cultures (500 ml) using an inexpensive carbon source, corn syrup (FIG. 3). A 50 ml, 12 day GB2 culture that was grown on GBM 50 mM HEPES and 80 ml/l GBH was transferred to a 2 liter flask, diluted 1:10 with GBM-50 mM HEPES, and supplemented with corn syrup to a final concentration of 20 mL/L. The GB2 culture was introduced and was incubated at 29° C. under constant stirring at 150 rpm for three days. Growth was monitored turbidometrically at 600 nm and optical parameters were quantitated by CGC-FPD. Results of this example are shown in FIG. 3. During this process, the MPA produced from IMPA is degraded by the invention for the inorganic phosphate it yields to meet the phosphorus demands of the culture. This property is an inherent characteristic of the consortium; no additional inoculum is needed for MPA mineralization because sufficient bacteria remain suspended in the effluent from the first bioreactor to serve as the inoculum for the second reactor. Commercial corn syrup solids preparations (e.g. MALTRINS) also provided an inexpensive carbon source for the invention which resulted excellent organophosphonate mineralization (FIG. 4 and 5).

Bioflims on Solid Surfaces

The GB2 consortium forms biofilms on solid surfaces when cultured in the presence of hydrolyzed Sarin. This property could be utilized to conveniently accumulate biomass on solid surfaces to improve hydrolyzed Sarin biodegradation rates.

It should be apparent that many modifications may be made to the above-described embodiments and still come within the spirit and scope of the present invention. Thus, the present invention is not limited by the above-described embodiments, but rather by the claims appended hereto.

What is claimed is:

1. An isolated and defined bacterial consortium GB2 of biologically pure cultures, said consortium GB2 having ATCC accession number 202200.

2. The bacterial consortium of claim 1, wherein said consortium GB2 is useful for the biodegradation of alkylphosphonates.

3. The bacterial consortium of claim 1, wherein said consortium GB2 comprises the bacteria *Methylobacterium radiotolerans* GB21; *Klebsiella oxytoca* GB2CS; *Agrobacterium tumefaciens* GB2GA; Aureobacterium GB2; and three strains of unclassifiead bacteria GB23, GB292, and GB 272.

* * * * *